Figure 1:
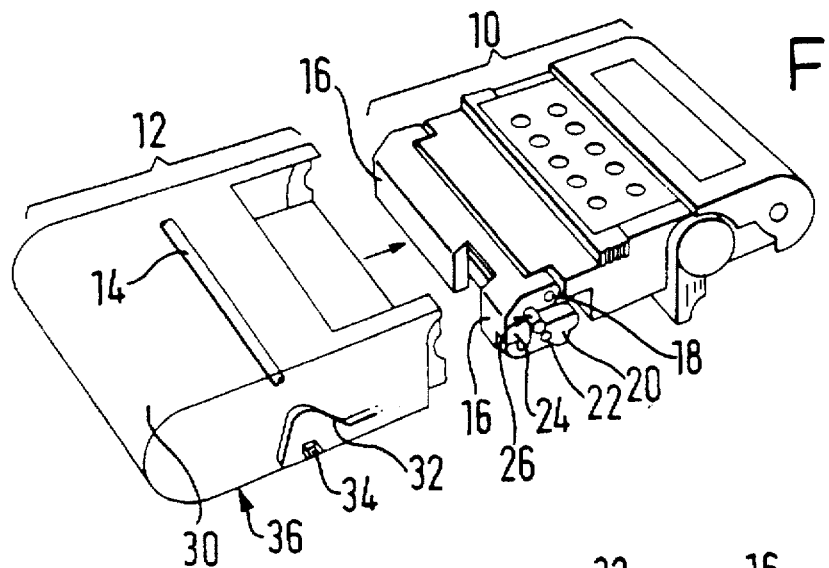
Figure 2:
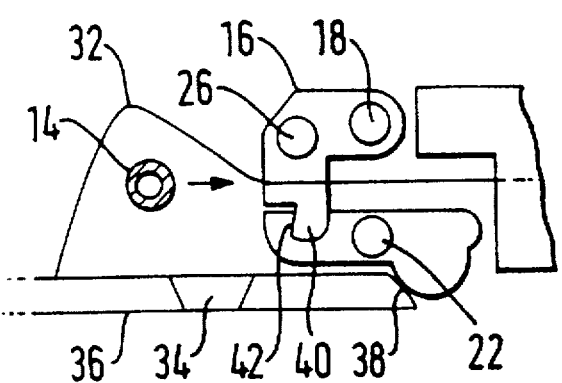
Figure 3:
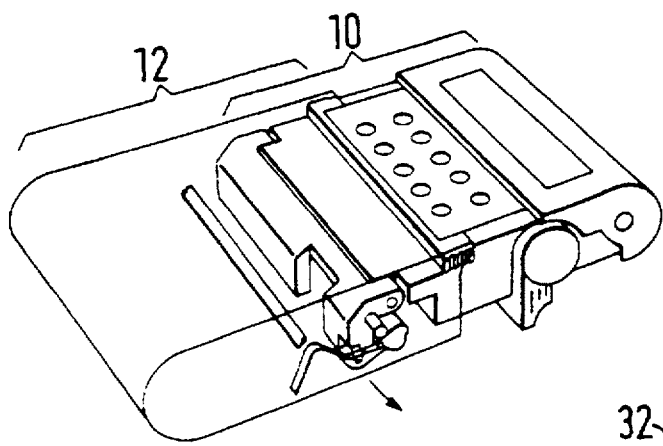
Figure 4:
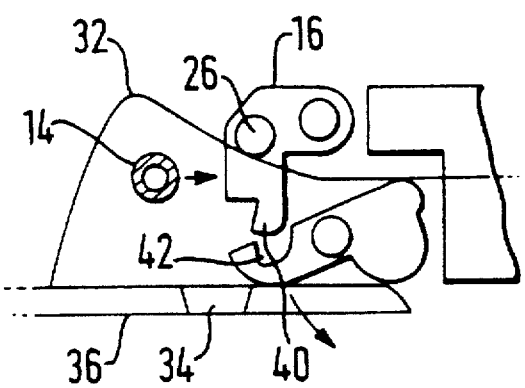
Figure 5:
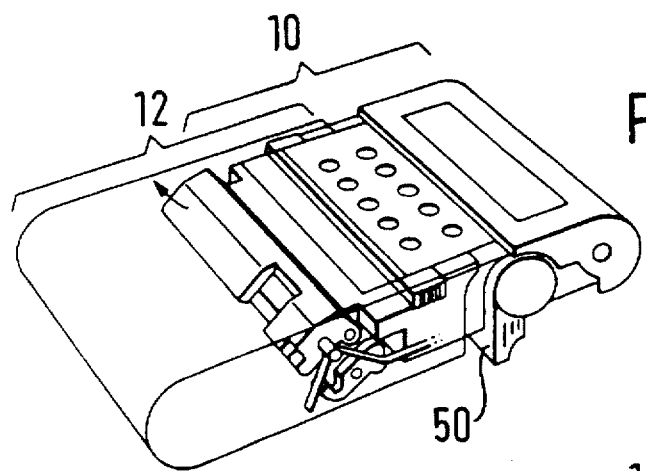
Figure 6:
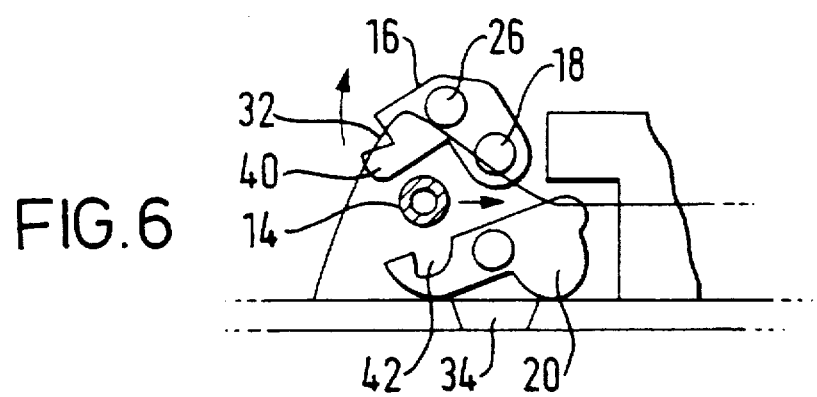
Figure 7:
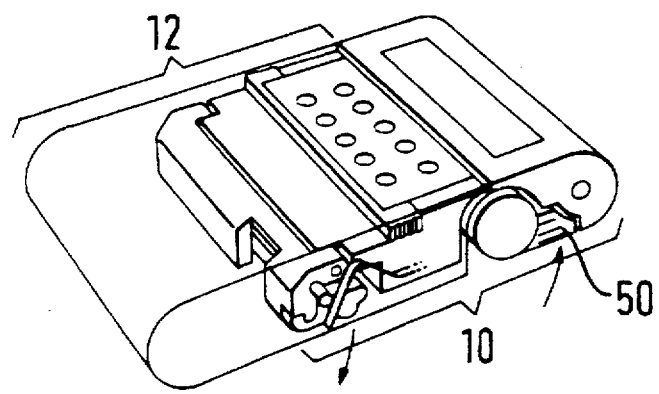
Figure 8:
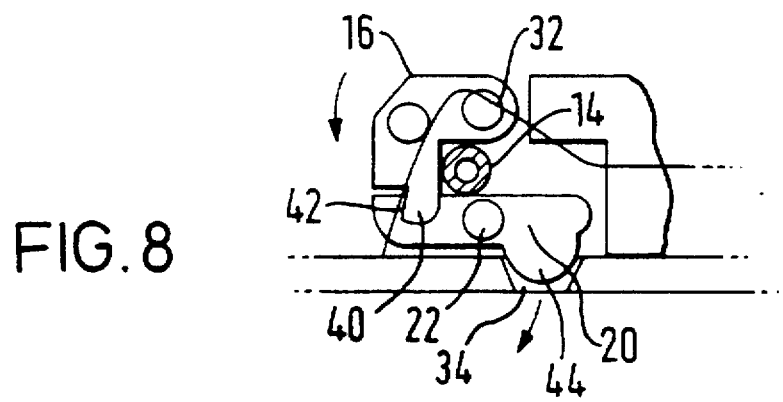

United States Patent [19]
Hilborne

[11] Patent Number: 5,755,691
[45] Date of Patent: May 26, 1998

[54] MEDICAL INFUSION PUMPS

[75] Inventor: David Graham Hilborne, Dunstable, United Kingdom

[73] Assignee: Graseby Medical Limited, Hertfordshire, United Kingdom

[21] Appl. No.: 669,418

[22] PCT Filed: Dec. 23, 1994

[86] PCT No.: PCT/GB94/02811

§ 371 Date: Jul. 1, 1996

§ 102(e) Date: Jul. 1, 1996

[87] PCT Pub. No.: WO95/17913

PCT Pub. Date: Jul. 6, 1995

[30] Foreign Application Priority Data

Dec. 30, 1993 [GB] United Kingdom ............... 93 26 555
Mar. 15, 1994 [GB] United Kingdom ............... 94 04 957

[51] Int. Cl.$^6$ .................................................. A61M 37/00
[52] U.S. Cl. ........................... 604/151; 604/131; 417/474
[58] Field of Search .................... 417/474, 478–480, 417/477.11, 477.2; 604/131, 151

[56] References Cited

U.S. PATENT DOCUMENTS 4,469,481 9/1984 Kobayashi ...................... 604/151
4,527,323 7/1985 Dawson ........................... 417/477.1
4,561,830 12/1985 Bradley ............................. 417/474
5,017,059 5/1991 Davis ................................. 417/474
5,088,904 2/1992 Okada ............................... 417/474
5,511,951 4/1996 O'Leary ............................ 417/474

Primary Examiner—Sam Rimell
Assistant Examiner—Luke J. Yeh
Attorney, Agent, or Firm—Price, Heneveld, Cooper, DeWitt & Litton

[57] ABSTRACT

A two part medical infusion pump comprises a first portion incorporating a pump mechanism, a pump control system, and a tube support, and further comprising a second portion arranged for detachable mounting to the first portion. The second portion carries a fluid-containing cassette and an associated fluid delivery tube. The tube support is arranged to be automatically moved out of a path of the fluid delivery tube as the first and second portions are moved towards an engagement position. The pump mechanism is arranged to compress the fluid delivery tube against the tube support of the first portion when the second portion is in the engagement position, such that controlled delivery of the fluid in the cassette to a patient is affected.

11 Claims, 3 Drawing Sheets

MEDICAL INFUSION PUMPS

The present invention relates to medical infusion pumps and more particularly to two-part medical infusion pumps comprising a first part incorporating a pump mechanism and control systems, and a second part, intended for detachable mounting upon the first part, incorporating a fluid cassette and a fluid delivery tube for fluid contained within the cassette.

The second part, incorporating the fluid cassette and delivery tube may, but need not be, a disposable item.

A positive, locking engagement between the first and second parts of the infusion pump is necessary, to ensure that the delivery tube of any second part fitted to the first part, is properly positioned for engagement by the pump mechanism of the first part, in order to ensure accurate, repeatable and controllable delivery of infusion fluid from the cassette via the delivery tube.

FR 2, 623,529 (Celsa) shows a two-part medical infusion pump according to Prior art. The part containing the fluid and fluid delivery tube has to be aligned into engagement with the part containing the pump mechanism by hand, and a support for the fluid delivery tube must also be subsequently located and secured manually.

The present invention provides an improved positioning and retaining means for the delivery tube of a two-part medical infusion pump incorporating such means, in which the delivery tube is carried by the second part, and the tube support means by the first part, of said two-part infusion pump.

Figure 9:
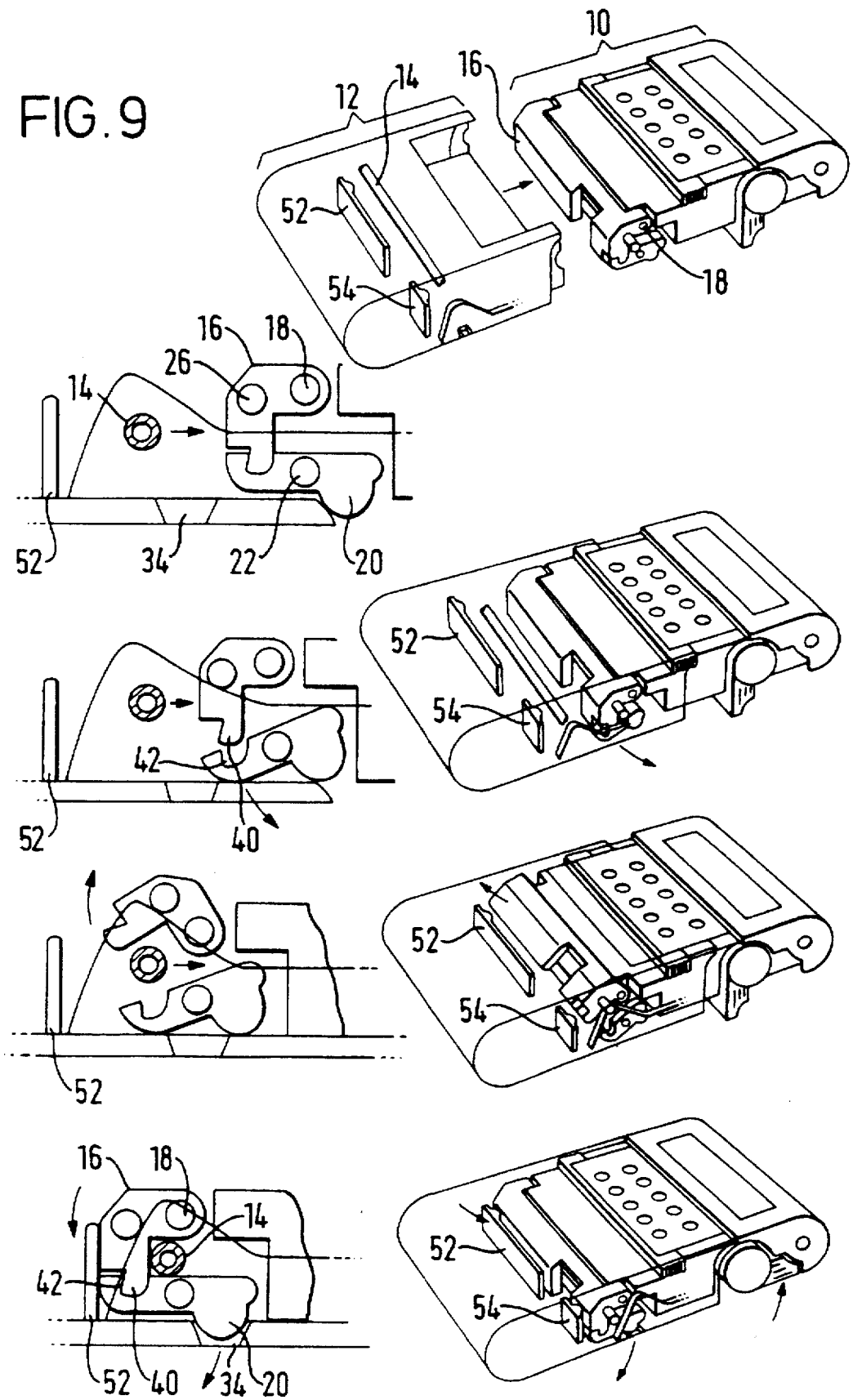

The invention will be described with reference to the specific embodiment shown in the accompanying drawings of which:

FIGS. 1, 3, 5 and 7 show, respectively, in perspective, the first and second parts of a two-part medical infusion pump steps in progressive steps of engagement;

FIGS. 2, 4 6, and 8 show corresponding diagrammatic end-elevation views of the operative elements of the two parts at each step; and FIG. 9 shows another embodiment.

Referring to the drawings, a two-part medical infusion pump comprises a first part 10 incorporating a pump mechanism and control systems, and a second part 12 containing a fluid cassette (not separately shown) and a flexible delivery tube, shown in part and diagrammatically as 14, connecting the fluid cassette to a patient for delivery of the infusate.

To deliver infusate to a patient it is necessary to introduce into, and correctly support the delivery tube 14 within, part 10 containing the pump mechanism, which may be of one of a number of types, operating to displace accurate volumes of infusate from the cassette by successive compressions of the delivery tube 14.

The introduction and support of the delivery tube 14, together with the locking of the support means, is achieved in the manner described below.

The body of part 10 has pivotally mounted upon it in the manner shown a tube support 16, pivoted upon pivot 18, and a latch 20 pivoted upon pivot 22. The end face 24 of tube support 16 mounts a projecting pin 26, adapted to act as a cam follower.

The body casing 30 of part 12 of the infusion pump is provided with an integrally formed track 32 and a detent 34 in the positions shown on its inside lower face 36.

The mechanism functions in the following manner:

1. part 12 is brought into initial engagement with part 10;
2. the tapered leading edge 38 of casing 30 of part 12 engages the nearer edge of latch 26, which is at this stage still locked in engagement with tube support 16, by means of the inter-engagement of tongue 40 within detent 42 of latch 26;
3. as part 12 is brought further into engagement with part 10, latch 20 is pivotted anti-clockwise about pivot 22, causing detent 42 to disengage from tongue 40 of tube support 16, as pin 26 engages with track 32 of casing 30;
4. further engagement of the two parts 12 and 10 causes tube support 16 to pivot clockwise as pin 26 continues to follow track 32, allowing tube 14 to enter the gap between the inner face of tube support 16 and latch 20;
5. at the fullest extent of engagement of parts 12 and 10, the lower part 44 of latch 20 falls into detent 34 of casing 30, and pin 26 rides over the highest part of track 32 and down the further side, allowing tube support 16 to rotate anti-clockwise, repositioning tongue 40 in detent 42 of latch 20.

In this way a) tube 14 has been accurately disposed along the inner face of tube support 16, to permit pumping of infusate by mechanical compression of delivery tube 14 against that inner face of tube support 16 by the pump mechanism contained within part 10; and b) the tube support 16 has been locked into position to resist displacement by the pump mechanism, by the inter-engagement of tongue 40 of tube support 16 and detent 42 of latch 20, latch 20 being engaged in detent 34.

When full engagement of parts 10 and 12 is complete, they are latched together by latch means not herein described, by rotating latch handle 50 into alignment with the the body wall of part 10.

To disengage the parts 10 and 12 from one another, latch handle 50 is rotated clockwise to lie at right angles to body 10, and part 12 is drawn away from part 10, causing tube support 16 and latch 20 to disengage in a manner the reverse of that described, allowing delivery tube 16 to be removed from the region of tube support 16, and allowing part 12 as a whole to be removed and replaced with another.

It will be apparent that various modifications may be made to the embodiment described, within the scope of the invention.

For example, with reference to FIG. 9 of the appended drawings, to ensure positive engagement of the two parts 40 and 42 of the latching mechanism which holds together the body parts 10 and 12, and locks tube support 16 into position with tube 14 disposed upon its inner face, means such as abutments 52/54 may be provided within the body part 12.

Abutments 52/54, which may each have a forwardly extending rib or ribs, are positioned within body part 12 such that they engage the outer face of part 16 when body parts 10 and 12 are fully engaged, ensuring part 16 rotates sufficiently anticlockwise as viewed in the drawings, to ensure tongue 40 of tube support 16 engages with detent 42 in the upper face of latch 20.

Use of the abutments 52/54 permits any necessary slight compression of tube 14 by tube support 16 to permit closure of the latch assembly as described, allowing tube support 16 to be fitted either with a weaker spring than would otherwise be necessary, or even with no spring.

The purpose of such a spring, which would generally be necessary in the absence of abutments 52/54, is to cause counter-clockwise rotation of tube support 16 about pivot 18 viewed from the end shown in the drawings, tending to maintain tube support 16 in the closed and latched position before, after, and during full operative engagement of case parts 10 and 12. Normally the latch 20 will be fitted with a spring causing clock-wise rotation of the latch such that there is positive downward engagement of the latch into detent 34, and upward of detent 42 with tongue 40.

The interengagement and disengagement of case parts 10 and 12 when abutments 52/54 are provided within part 12, generally as described with reference to FIGS. 1 to 8, is illustrated in FIG. 9, with like parts bearing the same reference numerals.

Abutments 52/54 may be replaced by a single abutment, without changing the principle of operation, but both are provided in the embodiment described in order to respectively engage the two parts of the outer face of tube support 16, one each side of the aperture therein.

The abutments, or abutment, may be moulded as part of the case part 12 or be attached to it, and may be upstanding from the lower face, be downwardly depending from the upper face, or may bridge the two faces.

A latching mechanism such as is described in relation to the drawings accompanying the specification may be fitted to one or to both sides of the first part 10 and the second part 12 of the infusion pump described.

I claim:

1. A two-part medical infusion pump comprising a first portion (10) incorporating a pump mechanism, a pump control system, and a tube support (16), and a second portion (12) arranged for detachable mounting to the first portion (10), the second portion (12) carrying a fluid-containing cassette and an associated fluid delivery tube (14);

characterised in that the tube support (16) is arranged automatically to be moved out of a path of the fluid delivery tube (14) as the first and second portions (10, 12) are moved towards an engagement position, and in that the pump mechanism is arranged to compress the fluid delivery tube against the tube support (16) of the first portion (10) when the second portion is in the engagement position, such that controlled delivery of the fluid in the cassette to a patient is effected.

2. A pump as claimed in claim 1 in which the tube support (16) is arranged automatically to pivot out of the path of the fluid delivery tube (14) as the first and second portions (10, 12) are moved towards the engagement position.

3. A pump as claimed in claim 1 or claim 2 in which the tube support (16) is caused to move out of the path of the fluid delivery tube (14) by a camming action, a cam follower (26) of the tube support (16) following a cam trace (32) of the second portion (12) as the first and second portions (10, 12) are moved towards the engagement position.

4. A pump as claimed in claim 3 in which the tube support (16) rests in an operational position against an abutment (52, 54) of the second portion (12).

5. A pump as claimed in claim 4 in which the abutment (52, 54) urges the tube support (16) in to the operational position, behind the fluid delivery tube (14), as the first and second portions (10, 12) approach the engagement position.

6. A pump as claimed in claim 1 in which a spring urges the tube support (16) into an operational position, behind the fluid delivery tube (14), as the first and second portions (10, 12) approach the engagement position.

7. A pump as claimed in claim 3 in which the camming action urges the tube support (16) into an operational position, behind the fluid delivery tube (14), as the first and second portions (10, 12) approach the engagement position.

8. A pump as claimed in claim 1 in which the tube support (16) is latched in an operational position by a sprung latch member (20).

9. A pump as claimed in claim 8 in which the latch member (20) is arranged to unlatch from the tube support (16), as the first and second portions (10, 12) are moved towards the engagement position, by virtue of the engagement of a part (44) of the latch member (20) with the second portion (12) of the pump.

10. A pump as claimed in claim 9 in which the said part (44) of the latch member (20) is located by a detent (34) of the second portion (12) when the latch member is in the latched position and the tube support (16) is in the operational position.

11. A pump as claimed in claim 1 including means (50) for securely latching the first and second portions (10, 12) together, in the engagement position.

* * * * *